Aug. 26, 1941. C. J. VAN BOURGONDIEN Plant Pat. 487
FREESIA PLANT
Filed April 29, 1941
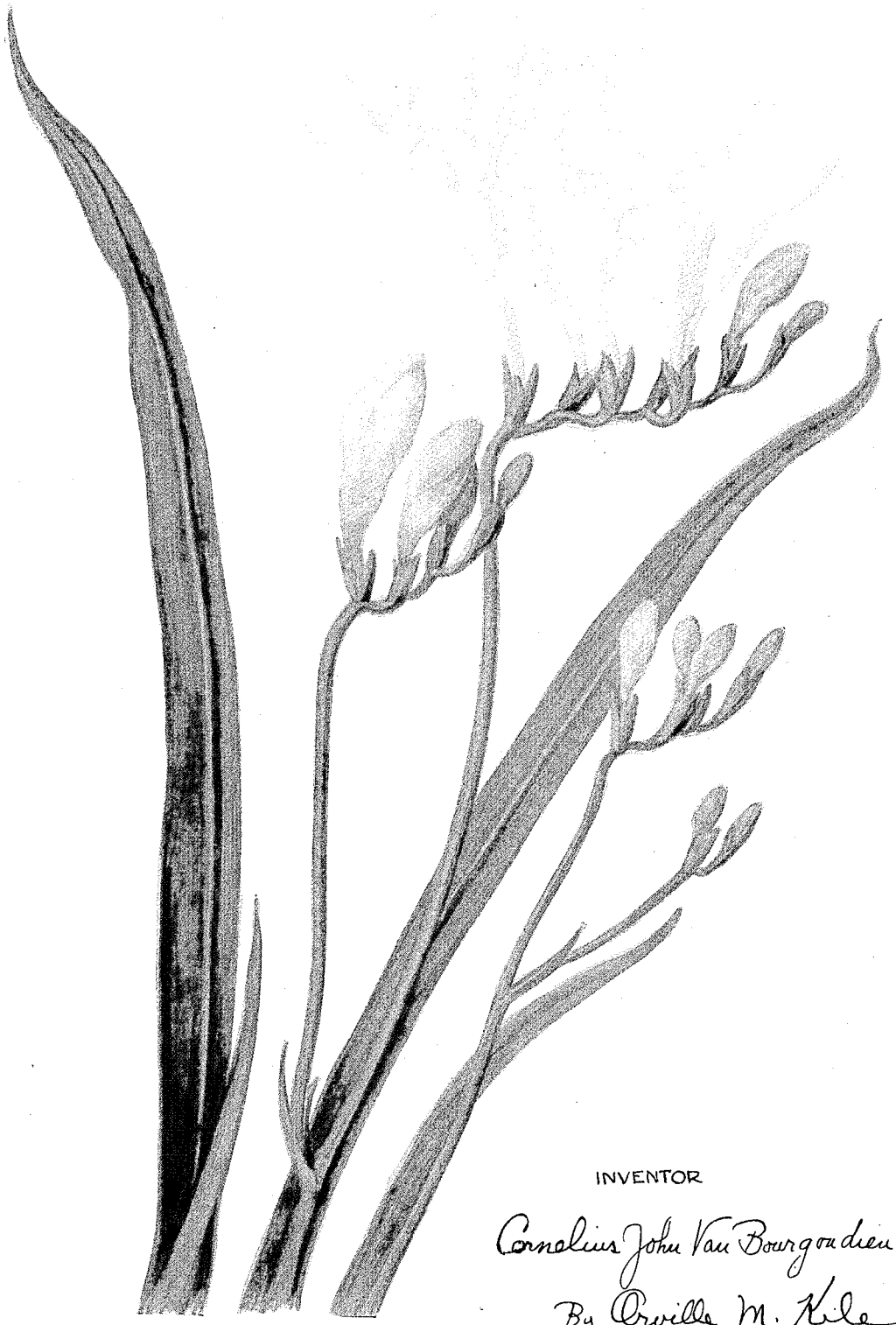
INVENTOR
Cornelius John Van Bourgondien
By Orville M. Kile
PLANT PATENT AGENT Patented Aug. 26, 1941

Plant Pat. 487

UNITED STATES PATENT OFFICE

487

FREESIA PLANT

Cornelius John Van Bourgondien, Babylon, N. Y., assignor to C. J. Van Bourgondien, Inc., Babylon, N. Y.

Application April 29, 1941, Serial No. 391,010

1 Claim. (Cl. 47—60)

My present invention relates to improvements in freesia varieties and falls in the class known as giant freesias. The principal object of my invention is to produce a freesia variety which is sturdy and tall, which has a long blooming reason, and which produces large blossoms predominantly white and of good substance.

My new variety is a seedling resulting from definite breeding efforts carried on by me, its seed parent being Albatre Supreme and its pollen parent the variety Fairy. It has been asexually reproduced for several years and its principal qualities have proved to be permanently fixed.

This new variety is recognized as being superior, as it received a first prize at the International Flower Show in March, 1941, over all other white varieties.

An outstanding feature of the variety is its very long blooming season. The first blossoms are usually cut about January 15th and plenty of blossoms are still available during the first week in April, making a blooming season of approximately three months. Also outstanding is the firm and fleshy substance of its blossoms, which feature enables them to last exceptionally long and to be shipped to excellent advantage. The plant grows unusually tall and is very sturdy—more so than any white freesia now on the market. The foliage is shorter in proportion to the flower stems than in other white varieties and does not interfere with cutting the flowers.

The original illustration accompanying this application shows a blooming spike with several branches, together with some of the foliage. It is impossible, however, for the artist to show the waxy-white appearance of the open blossoms.

Following is a detailed description of the plant and flower of this new variety. Color plate references are to Ridgeway's Color Standards and Nomenclature.

*The plant*

Growth: The growth of this new variety is very strong and sturdy and the plant is very productive of flowers. In almost every instance there are lateral branches on each stem, the blossoms of which open subsequent to those on the principal stem. Plants produced from full grown corms attain a height of about 36 inches.

Corms: Very large both in size and number, often producing as many as 15 or 16 to the plant.

Stems: The main flower stem is approximately 24 inches in length—about 8 inches from highest lateral branch to flower head. The principal flower stems are very thick, strong and upright and hold the flowers well above the foliage. Their sturdiness is very marked.

Foliage: Unusually abundant; leaves usually in clusters of 3 or 4; Parrot Green (Plate VI); narrow and spearlike, averaging ⅝ inch in width at their broadest point; taper gradually, ending in a sharp point; flat with midrib very prominent; 12 to 15 inches high, the flowers growing much above the foliage; proportionately shorter than foliage of other white varieties.

*The flower*

Arrangement: The flowers of a single stem or spike are borne in an upright position along a jointed rachis which is only slightly irregular and is bent almost at right angles to the stem in such a way that the first blossom of the group appears to be a vertical extension of the stem or peduncle. From four to seven blossoms are found on each spike and they are spaced from ⅜ to ½ inch apart on the rachis, this spacing being very close for flowers of such great size. Two to four of the blossoms on each spike are open at one time, with the remaining buds in varying stages of opening.

Sepals: Two; broad; sheath-like; slightly more than ½ inch in length; approximately Parrot Green (Plate VI).

Form: The perianth is long and funnel-shaped, with very little constriction of the throat which is long and tapering. Petals are gently curved and spread in lily-like form, seldom spreading at right angles to the throat.

Size: Very large; length approximately 3 inches; spread when fully open, 2¼ to 2½ inches.

Fragrance: Slight; delicate.

Petals: Six; very firm and substantial; waxy in appearance; lobes broadly oval, with gently rounded tip; sometimes overlapping; do not reflex or fold at midrib.

Color: The general color effect of the newly opened blossoms is pure waxy white with a very slight tint of Vinaceous Lavender (Plate XLIV). This lavender tint is most strongly evident in the opening buds. As the flower opens the tint on the outer surface becomes lighter and finally disappears entirely on most specimens. No lavender whatever is visible on the inside surface of the petals. The inside of the throat is from Light Cadmium to Lemon Chrome (Plate IV) and because of the translucence of the petals, the outside of the throat appears to be approximately Naples Yellow (Plate XVI). The petal opposite the stamens usually bears a slight splotch of Light Cadmium. When plants are grown at a temperature of 60 degrees the mature flower is completely waxy-white with a golden yellow throat, but it may have a slight lavender tint on the outer surface if grown at a temperature of 46 to 50 degrees.

Keeping quality: This variety keeps exceptionally well, probably due to the firm substance of the flowers. This quality makes it an excellent shipper.

Reproductive organs:

*Stamens.*—Three. Filaments arise from the throat, extend up one side of the perianth and are topped by gracefully curved gray anthers. The lower parts of the filaments are yellow and are attached to the sides of the throat. But extending from the top of the throat for ¾ to 1 inch, the filaments are free and of a pure white color.

*Pistils.*—Compound, with six branches; white; free the entire length; situated amidst the stamens but arising considerably above them.

*Comparison*

The known variety which is most nearly like my new variety is the subject of Plant Patent No. 237, commercially known as Schroeder's White. The principal differences between these two varieties are as follows:

1. The flower of my new variety habitually spreads at a lesser angle.

2. The petals of my new variety are smooth and round-tipped, with no reflexing or folding at the midrib. Those of No. 237 are inclined to be pointed at the tip and this effect is heightened by their tendency to fold at the midrib and reflex at the tip.

3. Absolutely none of the lavender tint is visible on the inner surface of the flowers of my new variety, the same not being true of No. 237. Also, the lavender tint on the outer surface of the open flowers of my variety is much lighter than that in similar position on No. 237 and in most specimens fades entirely as the blossom ages. Therefore the flowers of my variety have much more the effect of a pure white flower and very much resemble a waxy, white lily.

4. The flowers of my variety are larger than those of No. 237.

5. The flowers of my variety have much firmer substance, their lasting quality being approximately 25 percent greater than that of No. 237.

6. The plan of my variety is taller than No. 237 and other white varieties, although the foliage is no taller and does not interfere with flower cutting.

7. My variety produces a greater quantity of larger corms and is therefore more easily reproduced.

Having thus disclosed my invention, I claim:

The new and distinct variety of giant freesia plant herein shown and described, characterized particularly by its large and vigorous growth; its prolific production of very large corms; its exceedingly sturdy, tall and upright flower stems; its prolific production of very large, fleshy flowers having particularly splendid keeping qualities; its exceptionally long blossoming season; and the excellent substance and predominantly waxy-white, lily-like appearance of its flowers as indicated.

CORNELIUS J. VAN BOURGONDIEN.